(12) United States Patent
Bethke

(10) Patent No.: US 9,001,970 B2
(45) Date of Patent: Apr. 7, 2015

(54) METHOD AND DEVICE FOR IDENTIFYING UNKNOWN SUBSTANCES IN AN OBJECT

(71) Applicant: Johannes Bethke, Enter (NL)

(72) Inventor: Johannes Bethke, Enter (NL)

(73) Assignee: Entech Scientific B.V., Enschede (NL)

( * ) Notice: Subject to any disclaimer, the term of this patent is extended or adjusted under 35 U.S.C. 154(b) by 121 days.

(21) Appl. No.: 13/922,818

(22) Filed: Jun. 20, 2013

(65) Prior Publication Data

US 2013/0343525 A1 Dec. 26, 2013

(51) Int. Cl.
*G01N 23/203* (2006.01)
*G01N 23/20* (2006.01)

(52) U.S. Cl.
CPC ........ *G01N 23/203* (2013.01); *G01N 23/20091* (2013.01); *G01N 2223/643* (2013.01)

(58) Field of Classification Search
USPC ...................................................... 378/86–90
See application file for complete search history.

(56) References Cited

U.S. PATENT DOCUMENTS

| 4,887,285 | A | 12/1989 | Harding et al. |
| 5,428,657 | A | 6/1995 | Papanicolopoulos et al. |
| 5,666,391 | A * | 9/1997 | Ohnesorge et al. ............... 378/7 |
| 2013/0208850 | A1 * | 8/2013 | Schmitt ............................ 378/4 |

FOREIGN PATENT DOCUMENTS

EP 2075570 A 7/2009

* cited by examiner

*Primary Examiner* — Hoon Song
(74) *Attorney, Agent, or Firm* — Robert A. Jensen; Jensen & Puntigam, P.S.

(57) ABSTRACT

The present invention relates to a method and a device for identifying unknown substances in an object. According to the state of the art a collimated X-ray beam is directed onto the object and X-ray energy scattered from the object is detected and measured. The measurement values detected are compared to known measurement values corresponding to specific substances or classes of substances to identify unknown substances in the object. The method and device further execute the following steps: Detect and measure a function of Rayleigh intensity at a number of angles in a predetermined angular range to determine the angular course of the function of Rayleigh intensity in the angular range, Determine an angle or angle interval within the angular range at which the function of Rayleigh intensity is essentially zero; and identify unknown substances in the object by comparing the angle or angle interval determined to known angles or angle intervals at which the function of Rayleigh intensity corresponding to specific substances or classes of substances is essentially zero.

12 Claims, 2 Drawing Sheets

METHOD AND DEVICE FOR IDENTIFYING UNKNOWN SUBSTANCES IN AN OBJECT

TECHNICAL FIELD

The present invention relates in general to a method and device for identifying unknown substances in an object.

The present invention has for its purpose to provide such a method and device that are suitable for many different fields of application.

The unknown substances can be substances of interest, unexpected, suspicious or even unwanted substances depending on the application.

BACKGROUND OF THE INVENTION

One important field is formed by the security inspection of luggage at travel points, such as airports. When considering luggage inspection identifying the unknown substances is especially challenging as they are always lying behind a barrier, formed by a suitcase or bag, and may even be concealed in a container. Classic examples of unknown substances that are to be identified in luggage are contraband and dangerous materials, such as explosives. One important class of unwanted substances in luggage is formed by liquid explosives. The challenge is further enlarged as in air ports time is an essential factor, putting severe constraints on the method and the device with respect to a short turnaround and a low false rate.

Summarizing in the field of luggage inspection there exists an urgent need for fast and reliable identification of unknown substances, especially explosive liquid materials that are present behind a barrier and/or concealed in a container.

The present invention aims at providing a solution to this problem with the method according to the preamble of claim 1 and the device according to the preamble of claim 7.

Such a method and device are known in the field from U.S. Pat. No. 5,428,657. The known method allows for discrimination between materials, specifically used as basis for poultry screening. Three types of material, bone, fat and poultry meat are discriminated in order to keep the poultry meat bone free. The known method uses X-ray scattering, particularly the Rayleigh scatter in forward scattered geometry under small angles and also backscattered signal such as the Compton signals or as a cross check the Rayleigh—Compton ratio. For the analysis of bone use is made of forward scattered Rayleigh signal under small angles, around 5 degrees, completely penetrated through the material.

It is noted that another method for identifying unknown substances in an object is known from EP2075570. The known method is based on X-ray Diffraction (XRD) techniques. Generally, however, XRD is a method for determining crystalline materials while identification of the class of amorphous solids and moreover liquids is today seen as not generally solved. XRD, as said, being a suitable method for the investigation of predominantly crystalline material, is normally applied for lower X-ray energies (Cu, Mo, Ag as characteristic radiation and ≤60 kV high tension or voltage) as known for materials analysis. Here in the case of luggage control higher energies and higher tensions, for example 160 kV, are applied in order to penetrate through the luggage. The useful signals are here in the forward direction under small angles so that the known method works in transmission. In order to pinpoint materials more specifically and to enter into the realm of liquids, in the known method said diffraction profiles are taken under further investigation considering still finer and smaller details. Diffraction at amorphous materials generally is not governed by intrinsic peaks compared to crystalline substances. In the end there remains the challenge of significant signal strength and feature significance and differences in features from substance to substance in order to deduce the right information.

SUMMARY OF THE INVENTION

The method, respectively and the device, according the invention takes another approach that is described in the characterizing part of claim 1 respectively claim 7.

The method and device according to the invention are based on the insight that the angle dependent decay of the Rayleigh scattering provides a unique and reliable identification of substances, including liquids. Applicant is convinced that Transportation Security Administration (TSA) Type D demands for luggage inspection can be met by the method and device according to the invention. By measuring a number of points forming part of an angular course, the false rate can be effectively lowered. Throughput time can be saved, for instance by minimizing measurement time for each point and/or by simultaneous measurement at different angles using multiple detectors, thereby rendering the method and device useful not only for inspection of checked-in luggage, but for inspection of carry-on baggage as well.

The method and device according to the invention are complete angle dependent and offer significant, sometimes huge measurement signals that are easy to detect.

According to an additional embodiment as described in method claim 2, respectively device claim 8, unknown substances comprising mixtures of materials, such as liquid explosives with metal parts can be identified. It has been seen that for said mixtures a function of Rayleigh intensity asymptotically approaches a constant value not being zero.

According to yet a further preferred embodiment a gradient of the function of Rayleigh intensity is calculated to determine an angle or angle interval within the angular range at which the function of Rayleigh intensity is essentially zero. A gradient can be calculated based on a minimal amount of measuring points thereby saving time.

In a further advantageous embodiment X-ray back scattering techniques are used that offer the possibility of using the method and device in small spaces, or even producing a portable device.

In an embodiment that is especially suitable for luggage inspection X-rays are radiated having an energy that is sufficiently high to penetrate luggage barriers.

In a practical embodiment the angular range comprises angles between 30 and 140 degrees that allow for detection of most unwanted substances in luggage.

BEST MODE FOR CARRYING OUT THE INVENTION

Figure 1:
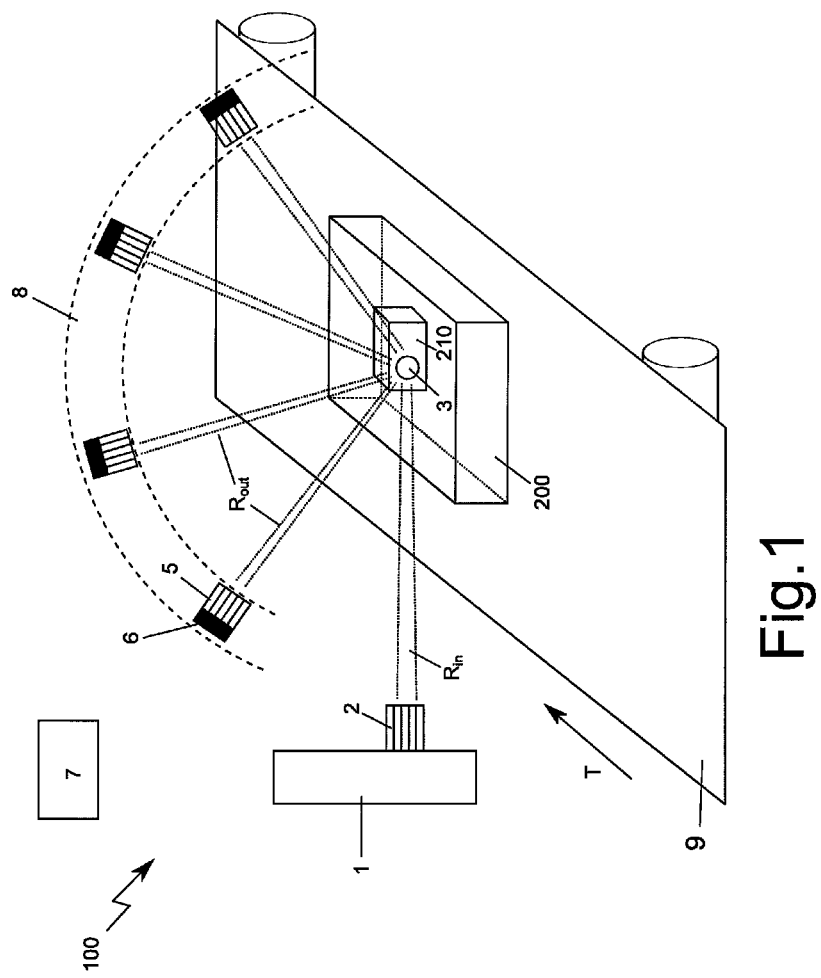
FIG. 1 shows a preferred embodiment of a device according to the invention.

In the preferred embodiment shown in FIG. 1 the device 100 according to the invention is arranged for luggage inspection. The object under inspection is a suitcase 200, wherein a container 210 filled with a liquid explosive is present. The suitcase 200 is transported on a conveyor belt 9.

Device 100 comprises an X-ray source 1 for radiating X-rays having an energy that is sufficiently high to penetrate barriers. Applicant believes that 50 to 100 keV or more will be sufficient. The preferred embodiment comprises a polychromatic X-ray source, more specifically a tungsten X-ray tube with primary high tension of 100 kV or 160 kV or even higher. Alternatively monochromatic X-ray radiation may be used, other X-ray tube anode materials may be chosen as well as other values for high tension of the tube. It is noted the method and device according to the invention are not restricted to the use of X-ray tubes. As an alternative a synchrotron is considered to be a suitable source for X-radiation as well.

The beam emerging from the X-ray source 1 is collimated by a first collimator 2 on the primary side of the optical path in order to define a substantially parallel beam $R_{in}$. Preferably the first collimator 2 is arranged to collimate the X-rays into a generally pencil shaped X-ray beam.

The outgoing radiation $R_{out}$ has a number of components and consists of transmitted radiation and X-ray diffracted signals and X-ray scattered signals emerging in an angular range. On the secondary side of the optical path one or more second collimators 5 may be positioned, each in front of an X-ray detector 6 in order to provide for a sufficient angular resolution during measurements.

The detectors 6 are arranged to detect the scattering of X-ray energy from the object 200. Preferably the detectors are arranged to detect the Rayleigh back scattering of X-ray energy from the object 200.

Preferably each detector is arranged to count X-ray events and to determine the corresponding energy to every count. Suitable detectors include a high-purity Ge detector or a CdTe/CdZnTe detector. In another aspect of the invention a multi segment Ge detector or multiple single Cd (Zn)Te detector may be used in order to gain measurement time. In the most advanced situation one or multiple pixellated detectors with many pixels, all pixels revealing an energy spectrum, will improve on measuring time such that a high throughput of objects is guaranteed.

The detectors 6 are preferably arranged to measure X-ray energy within an angle range of 30-140 degrees. One or more movable detectors can be used or an array of detectors or any combination thereof to deliver an angular dependent data set.

In the preferred embodiment shown an array of detectors 6 is arranged within a detector housing 8. The detectors 6 may be arranged movably within the detector housing 8 and/or the detector housing 8 itself may be movable. One or more additional detector housings 8 may be placed in transport direction T of the object 200.

In the preferred embodiment shown the device 100 according to the invention is arranged to inspect a region of interest or volume of interaction 3 within the object 200.

In an alternative embodiment (not shown) a fan beam geometry is introduced, wherein the first collimators are slit collimators. An area of detectors is formed with many rows of detectors, wherein every single detector accepts pencil beam like shaped rays. In this alternative embodiment a complete region of interest of a suitcase can be investigated in parallel. This again saves significant time and is suitable for hand baggage as well as for check-in baggage screening.

A processor 7 is arranged to receive the measured data from the detectors 6. The processor 7 is in communication with a memory in which a database is stored filled with information about the angle dependent behaviour of specific substances and/or classes of substances.

The processor 7 is arranged to identify unknown substances that are present within the region 3 based on comparison between the measured data and the data stored in the database using the method according to the invention.

In the following all steps of the method according to the invention are discussed.

Step 1: Directing a Collimated X-Ray Beam onto the Object

In a first step energy-dispersive X-ray spectroscopy (EDS or EDX) techniques are used to analyse the object. Various EDS or EDX devices known in the art will be suitable. A collimated X-ray beam is directed onto the object by an X-ray source for radiating X-rays having an energy that is sufficiently high to penetrate luggage barriers.

Step 2: Detecting and Measuring the Scattering of X-Ray Energy from the Object

In step 2 in general X-ray scattering spectra are detected. Preferably X-ray backscattered radiation is detected. X-ray scattering signals are known to be elastic and inelastic, referred to as Rayleigh and Compton scattering, respectively. According to the invention at least Rayleigh spectra are detected. The strength of the signals is dependent on the primary X-ray spectrum impinging on the object to be investigated. Furthermore the intensities of these signals are angle dependent.

Step 3: Detecting and Measuring a Function of Rayleigh Intensity at a Number of Angles in a Predetermined Angular Range to Determine the Angular Course of the Function of Rayleigh Intensity in the Angular Range According to the invention within a predetermined angular range an energy resolved spectrum is detected by the X-ray detector(s) and preferably recorded. The energy spectrum at each angle can contain Rayleigh (elastic) and Compton (inelastic) X-radiation of the characteristic (in this example: tungsten) radiation of the tube and also diffraction peaks stemming from crystalline material.

In step 3 in the scattered X-ray signals a function of the Rayleigh X-ray intensities of the W-radiation scattered by the unknown substance is determined. This function can be the Rayleigh (R) intensity itself or the Rayleigh-to-Compton ratio (R/C), which is the division of both signals or the Rayleigh to total Intensity (I) ratio (R/I=R/(R+C)). In the latter case advantageously no calibrations are necessary as compared to both known methods described in the introductory part. Alternatively mathematical operations of the above mentioned functions, e.g. a gradient or logarithm, may be determined and used as the function in step 3.

Applicant determines the course of those signals as a function of angle or as a function of a deduced measure of the angle. For instance, for normalization purposes one often takes the sin $\theta/\lambda$ ($\lambda$ being the X-ray wavelength) as a measure instead of the angle $\theta$ itself. The choice is made in order to optimize the determination and discrimination of substances and may be different for different substance classes and X-ray sources.

Step 4: Determining an Angle or Angle Interval within the Angular Range at which the Function of Rayleigh Intensity is Essentially Zero The invention is based on the insight that for a number of substances the Rayleigh intensity approximately vanishes at some point in the angular range. Different approaches can be chosen to determine the angular point or angular points of zero intensity. In a preferred embodiment a gradient of the Rayleigh and/or Rayleigh-to-Compton signals and/or the Rayleigh-to total-Intensity ratio is calculated from which said zero intensity can be determined.

The invention is based on the further insight that for specific material classes the angular points for which the signal or signal combination vanishes in approximation are lying essentially in a narrow angular interval. It appears that said specific material classes comprise dangerous materials like explosives, be it liquid or solid, and drugs. This further insight is used to determine the presence of unknown substances falling in said specific material classes in the object under inspection.

It is noted that throughout this text 'essentially zero intensity' is meant to comprise intensities actually reaching zero as well as intensities closely approaching zero. An intensity value is considered closely approaching zero when it falls below a predetermined threshold value. One suitable threshold value may be 3 a for the top value of a Gaussian curve, when said Gaussian curve is fitted through the intensity values.

Applicant refers to the angular points of zero intensity as 'k-points' (from key) and applicant refers to the method developed as 'k-point analysis'. The reason for the existence of said k-points can, among others, be understood by regarding the complete scattering function and its radiation components of a substance. As an example, not limiting generality, explosives often exhibit a pronounced content of nitrogen and constitute a class of substances exhibiting a special angular dependency of the scattering signals. Liquids and liquid explosives constitute other classes and exhibit other ranges of angular courses with corresponding other k-point intervals.

Step 5: Identifying Unknown Substances in the Object by Comparing the Angle or Angle Interval Determined Earlier to Known Angles or Angle Intervals at which the Function of Rayleigh Intensity Corresponding to Specific Substances or Classes of Substances is Essentially Zero.

Applicant finds it is possible to identify, pinpoint or determine the presence of (classes of) substances and in particular to find dangerous materials and contraband based on the above 'k-point analysis'. These classes and corresponding k-point data have been pre-determined by numerous experiments and tests resulting in a huge database.

EXAMPLES

Some examples following from experiments are presented in table 1 below. The experiments have been performed with a tungsten X-ray tube at 100 kV high tension.

| Material | k-points (in degrees) |
|---|---|
| Solid explosives | 60-70 |
| Plastics | 35-50 |
| Metals | 80-140 |
| Liquids | 40-80 |
| Liquid explosives | 60-70 |
| Acids | 70-85 |
| H2O | 60 |
| Orange juice | 55 |
| Coca Cola | 55 |

Table 1 shows materials and corresponding angular value(s) for which the intensity of the elastic component of the scattered X-ray radiation is essentially zero. In general the intensity can be represented by values of Rayleigh (R), Rayleigh/Compton (R/C ratio), a gradient or any other functional representation of scattered X-ray radiation.

Figure 2:
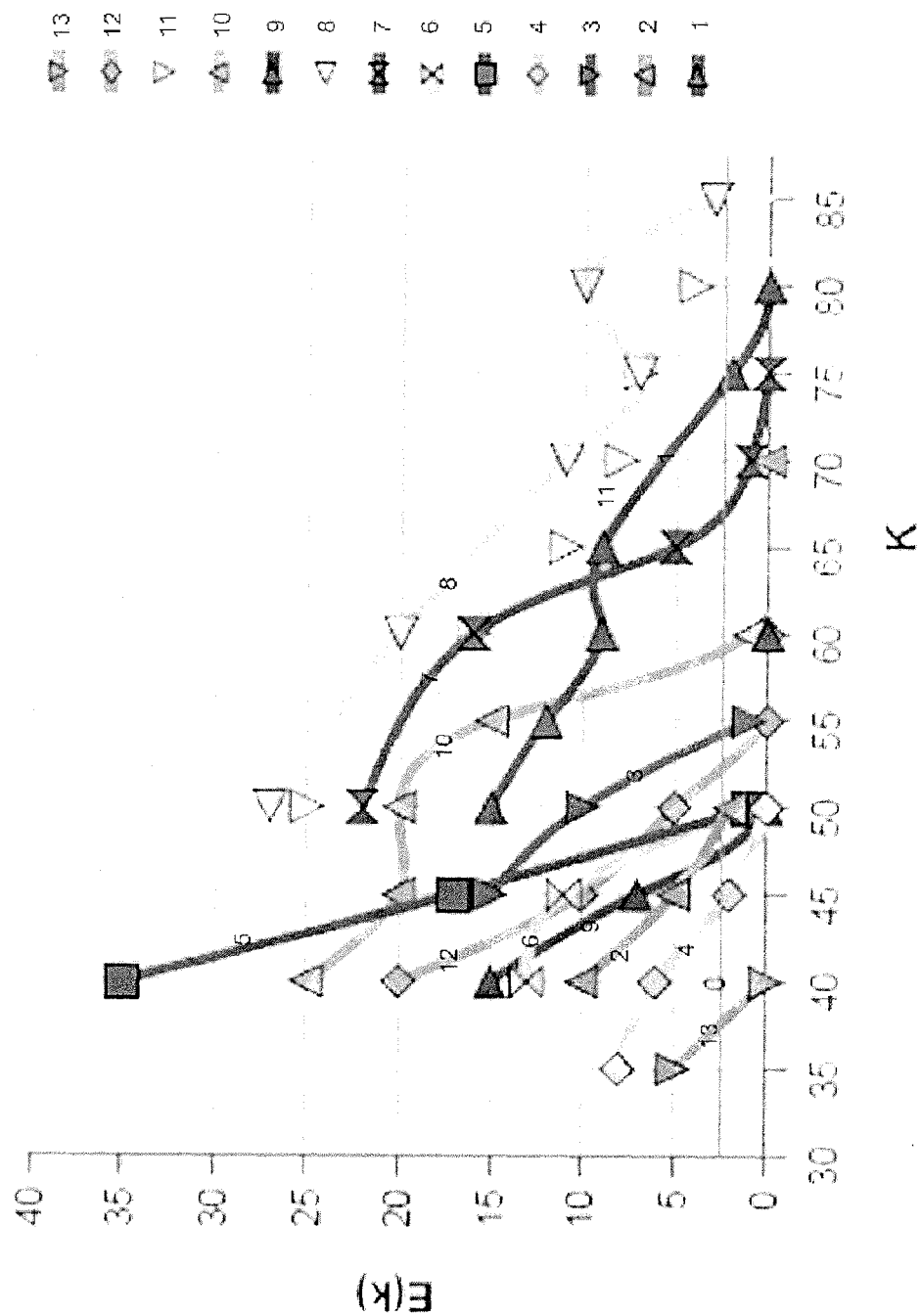
FIG. 2 shows a diagram of angular course showing angle dependent Rayleigh back scattering of X-ray energy from an object comprising various liquids.

FIG. 2 shows the angular course of a function of Rayleigh intensity E(k) for several liquids. The liquids are identified by number in the list below. From FIG. 2 it can be seen that liquids can be identified by their k-points.

1=sodium chloride solution
2=motor oil
3=olive oil
4=thinner
5=whiskey
6=whiskey in original bottle
7=nitric acid
8=phosphoric acid
9=petrol
10=water
11=hydrochloric acid
12=alcohol
13=empty plastic bottle Using the k-point analysis the material classes can be quickly pinpointed and then determined by comparison with the databank. For instance 'the nitrogen group', in which a number of solid and liquid explosives are contained, can be easily detected. With the k-point analysis a very important first decision can be made, and further, by an extended angular course additional information can be retrieved. For a number of crystalline materials additionally comparisons of diffraction peaks can be conducted. This can be used as a cross-check.

For an even more detailed determination the angular course and the k-points of unknown substances are compared in detail with said database by means of software algorithms.

Generally, the method according to the invention does not give the chemical, stoichiometric formula of the substance. In special applications, however, calibrations can be introduced for quantification purposes (in the sense of how much of a substance is present). This is often the case when there is pre-knowledge of the substances appearing in an object. This may be the case when the present substances are limited to a number of known classes or when classes can be excluded beforehand.

Although the method and device according to the present invention have been elucidated by referring to the described and shown preferred embodiment relating to luggage inspection, many other applications are possible. In general the method and the device according to the invention allow for clear identification of inhomogeneities, voids or differences in material composition of an object. All identification can be performed equally well when the object is placed behind barriers or in containers. Some specific examples include: corrosion inspection within tubes or pipelines, discrimination between different food components, such as bones and meat, identification of fake compositions when the object comprises precious metals, et cetera. For each application the specific values for tension and/or energy of the X-rays need to be suited to the barrier strength.

It is therefore noted that the invention is not limited to the embodiment described and shown herein, but generally extends to any embodiment which falls within the scope of the appended claims as seen in the light of the foregoing description and drawings.

The invention claimed is:

1. A method for identifying unknown substances in an object, comprising the steps of:
   a) Directing a collimated X-ray beam onto the object;
   b) Detecting and measuring X-ray energy scattered from the object;
   c) Comparing the measurements of step b) to known measurements corresponding to specific substances or classes of substances to identify the unknown substances in the object;
   Characterised in that the method further comprises the following steps:
   d) Detecting and measuring a function of Rayleigh intensity at a number of angles in a predetermined angular range to determine the angular course of the function of Rayleigh intensity in the angular range;
e) Determining an angle or angle interval within the angular range at which the function of Rayleigh intensity is essentially zero; and
f) Identifying the unknown substances in the object by comparing the angle or angle interval determined in step e) to known angles or angle intervals at which the function of Rayleigh intensity corresponding to specific substances or classes of substances is essentially zero.

2. A method according to claim 1, whereby in step e) no such angle interval nor angle can be determined within the angular range, the method comprises the following further steps:
   g) Detecting and measuring a function of Compton intensity at a number of angles in the predetermined angular range to determine the angular course of the function of Compton intensity in the angular range;
   h) Determining the Rayleigh-to-Compton ratio at a number of angles in the predetermined angular range; and
   i) Characterizing the unknown substances in the object as suspicious when the Rayleigh-to-Compton ratio <1.

3. A method according to claim 1, whereby step e) comprises the step of calculating a gradient of the function of Rayleigh intensity.

4. A method according to claim 1, whereby step b) comprises detecting a function of Rayleigh or Compton back scattering of energy from the object.

5. A method according to claim 1, whereby in step d) the angular range comprises angles between 30 and 140 degrees.

6. A method according to claim 1, whereby in step a) the X-ray beam comprises X-rays having an energy that is sufficiently high to penetrate luggage barriers, preferably with high tensions of 100 kV and higher.

7. A device for identifying unknown substances in an object, comprising:
   a) Means for directing a collimated X-ray beam onto the object;
   b) Means for detecting and measuring X-ray energy scattered from the object;
   c) Means for comparing the measurements of means b) to known measurements corresponding to specific substances or classes of substances to identify the unknown substances in the object characterised in that the device further comprises:
   d) Means for detecting and measuring a function of Rayleigh intensity at a number of angles in a predetermined angular range to determine the angular course of the function of Rayleigh intensity in the angular range;
   e) Means for determining an angle or angle interval within the angular range at which the function of Rayleigh intensity is essentially zero; and
   f) Means for identifying the unknown substances in the object by comparing the angle or angle interval determined by means e) to known angles or angle intervals at which the function of Rayleigh intensity corresponding to specific substances or classes of substances is essentially zero.

8. A device according to claim 7, wherein the means in step e) cannot determine such an angle interval nor such an angle within the angular range, further comprising:
   g) Means for detecting and measuring a function of Compton intensity at a number of angles in the predetermined angular range to determine the angular course of the function of Compton intensity in the angular range;
   h) Means for determining the Rayleigh-to-Compton ratio at a number of angles in the predetermined angular range; and
   i) Means for characterizing the unknown substances in the object as suspicious when the Rayleigh-to-Compton ratio <1.

9. A device according to claim 7, wherein the means e) are arranged to calculate a gradient of the function of Rayleigh intensity.

10. A device according to claim 7, wherein the means b) are arranged for detecting a function of Rayleigh or Compton back scattering of energy from the object.

11. A device according to claim 7, wherein the means d) are arranged such that the angular range comprises angles between 30 and 140 degrees.

12. A device according to claim 7, wherein the means a) comprise an X-ray source for radiating X-rays having an energy that is sufficiently high to penetrate luggage barriers, preferably with high tensions of 100 kV and higher.

* * * * *